United States Patent [19]

Armstrong

[11] Plant 4,301

[45] Sep. 12, 1978

[54] ROSE PLANT

[75] Inventor: David L. Armstrong, Orange, Calif.

[73] Assignee: Armstrong Nurseries, Inc., Ontario, Calif.

[21] Appl. No.: 843,139

[22] Filed: Oct. 17, 1977

[51] Int. Cl.[2] ..... A01H 5/00

[52] U.S. Cl. ..... Plt./15

[58] Field of Search ..... Plt./15

*Primary Examiner*—Robert E. Bagwill
*Assistant Examiner*—James R. Feyrer
*Attorney, Agent, or Firm*—Andrew R. Klein

[57] ABSTRACT

A new hybrid tea rose of the tall bush type, tender to half-hardy, raised as an outdoor seedling and useful primarily for garden decoration. One notable characteristic is the uniform medium golden yellow blooms, which are of large size (13 to 14 centimeters) and fragrant, with 25 to 34 petals plus 2 to 4 petaloids. The color lightens as the flower matures. The plant is vigorous and blooms abundantly.

1 Drawing Figure

This invention relates to a new variety of hybrid tea rose of the tall bush outdoor type which was raised as a seedling for garden decoration. The rose described herein was grown in Ontario, Calif., and the observations made generally relate to that climatic zone.

The seed parent of this new variety was "Buccaneer", U.S. Plant Pat. No. 1,119, and the pollen parent was "Peace", U.S. Plant Pat. No. 591.

The new variety may be distinguished from its seed parent Buccaneer by the size of its blooms, which range from 13 to 14 centimeters or about 5 to 5½ inches in diameter, as compared to 3 to 3½ inches for Buccaneer. Furthermore, there are more than twice as many pistils in the new rose, which has approximately 175, in comparison with 69 pistils in Buccaneer. Still further, the new rose plant has leaflets which are semi-glossy and which tend to be folded inwardly bilaterally from the midrib and tend to hang downwardly from the rachis, while Buccaneer has non-glossy, flat foliage.

As compared to its pollen parent, Peace, the new rose may be distinguished, inter alia, in that the flower size, although large (5 to 5½ inches in diameter) is somewhat smaller than the flowers of the Peace rose, which are approximately 6 inches in diameter. The number of petals in blooms of the new variety is substantially smaller, being from 25 to 34 petals, plus 2 to 4 petaloids, as compared to 40 to 45 petals with Peace. Freshly opened blooms of the new rose are golden yellow in color with no significant amount of other coloration of the petals, while freshly opened blooms of Peace have golden yellow petals distinctively edged with rose pink. The foliage of Peace is deep green and highly glossy, whereas the new variety is semi-glossy and has medium olive green coloration.

The plant holds its distinguishing characteristics through succeeding propagations by budding. It bears its flowers usually singly, but sometimes 2 to 3 or more on a single stem. The stems are strong and of medium to long length. The quantity of bloom is abundant, outdoors, and is nearly continuous during the growing season. The fragrance is moderate to strong, from tea to spicy.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is average in length, and average to heavy in caliper. It is erect, with numerous stipitate glands. Its color is between Strong Yellow Green, 5GY6/8, and Strong Yellow Green, 5GY7/10.

Before the calyx breaks, the size of the bud is medium to large, the length is medium, and the form is pointed and ovoid. There are small slender foliaceous appendages and stipitate glands on the surface of the bud, but no significant foliaceous parts extend beyond the tip of the bud.

As the calyx breaks, the color of the bud is near Vivid Yellow, 5Y8/12. The inner surface of the sepals has a fine tomentum, and the sepals usually turn down quickly as the bud opens.

As the first petal opens, the bud is from average to large in size, and ovoid to urn-shaped. The color, on both the inside and outside surfaces, is between Vivid Yellow, 2.5Y8/12, and Vivid Yellow, 5Y8/12. The bud opens up well and is not retarded or prevented from opening by cold, hot, wet, or dry weather.

BLOOM

When fully open, the bloom is large in size, from 13 to 14 centimeters in diameter. It has double petalage, with from 25 to 34 petals plus 2 to 4 petaloids, arranged regularly. In form, the bloom is high centered at first, becoming open, the petals at first somewhat tightly cupped, with tips reflexed, becoming later at maturity loosely cupped, with tips reflexed outward.

The petals are of medium thickness and texture. They are moderately leathery, with inside slightly velvety, and outside slightly shiny to satiny. The shape of the outside petals is round to broadly obovate. The intermediate petals are from nearly round to broadly obovate, while the inside petals are from nearly round to broadly obovate, or sometimes irregular in shape. The colors may be modified by being blotched, shaded and/or washed with other colors.

The following is a description of a newly opened flower from a rose grown outdoors in Ontario, Calif., in the month of September.

The outer surface of the outside petal ranges from a color between Vivid Yellow, 2.5Y8/12, and Brilliant Greenish Yellow, 7.5Y9/8, to a color significantly lighter than Brilliant Greenish Yellow, 7.5Y9/8, especially near the margins. The inner surface of the outside petal is the same coloration as the outer surface. The outer and inner surfaces of the intermediate petal are similar in color to the corresponding parts of the outside petal.

The outer surface and the inner surface of the inside petals range from Vivid Yellow, 2.5Y8/12, to Brilliant Greenish Yellow, 7.5Y9/8.

The following description was made from a rose which had been open for 3 days outdoors in the month of September in Ontario, Calif.

Inner and outer surfaces of both the outside and the inside petals all were generally lighter than but similar to the color values of the corresponding parts on the newly opened flowers.

The general color effect of the newly opened flower is a color ranging from Vivid Yellow, 2.5Y8/12, to Brilliant Greenish Yellow, 7.5Y9/8. The general color effect of the bloom which has been open for 3 days is a color ranging from between Vivid Yellow, 2.5Y8/12, and Brilliant Greenish Yellow, 7.5Y9/8, to a color significantly lighter than Brilliant Greenish Yellow, 7.5Y9/8.

The petals drop off cleanly, except for a few petaloids, and are not particularly affected by cold, hot, wet, or dry weather. The color fades to creamy yellow in hot sunlight.

The flowers last on the bush in the garden from 4 to 5 days in September, and cut roses grown outdoors but kept at living-room temperatures last from 3 to 4 days in September, in Southern California.

REPRODUCTIVE ORGANS

The stamens are of average number, arranged regularly about the pistils, with a few tucked in the calyx.

The filaments are medium length to long, and in color between Vivid Yellow, 5Y8/12, and Moderate Red, 2.5R4/10. Most are with anthers.

The anthers are medium in size, and all open approximately at once. Along the margins their color is between Moderate Orange Yellow, 10YR8/10, and Strong Orange Yellow, 7.5YR7/11. AT the center portion, the color is near Brilliant Yellow, 5Y9/9.

The pollen is moderate in amount and, in color, near Strong Orange Yellow, 7.5YR7/11.

There are many pistils, these being approximately 175 in number.

The styles are slightly uneven, average length and average caliper, and somewhat compactly bunched. They bear some red pigment just below the stigmas.

The stigma is near Moderate Orange Yellow, 7.5YR8/8, in color.

The ovaries are enclosed in and protruding from the calyx.

The hips are average length and globular, smooth, with thick fleshy walls. When fully mature, their color is between Strong Orange, 2.5YR6/12, and Strong Reddish Orange, 10R6/12.

The sepals are more or less permanent and medium-length and recurved. Their inner color is medium brown with light gray tomentum, while the outside is medium brown.

The seeds are few to average in number, about 8 to 20, and are medium size to large.

THE PLANT

Foliage

The compound leaves usually consist of 3 to 7 leaflets. They are normal to abundant, of medium to large size, moderately heavy to somewhat leathery and semi-glossy, sometimes with leaflets hanging downward. In shape, the leaflets are nearly round to ovate, with apex acute, base obtuse, and margin simply serrate, with some slight irregularities and a tendency to remain folded bilaterally inward from the midrib. The color of the mature leaf is near Moderate Olive Green, 5GY4/3, on the upper surface. The under surface is perhaps best characterized as "light grayish olive green."

The young leaves have an upper surface which is near Strong Yellow Green, 2.5GY6/8, moderately overlaid, especially near the margins, with near Dark Red, 5R3/7. The under surface of the young leaf is between Strong Yellow Green, 2.5GY6/8, and Brilliant Yellow Green, 5GY8/8, moderately overlaid with near Dark Red, 5R3/7.

The rachis is of average size. Its upper side is grooved, with hairs and stipitate glands on the edges. The underside is smooth, with fine hairs.

The stipules are medium-length to long, medium-width to wide, and with medium-length points turning out at an angle of less than 90°.

The plant possesses average resistance to mildew, when compared to other varieties in commerce under similar conditions.

GROWTH

In habit, the new cultivar is a bushy upright-spreading or semi-climbing plant, of vigorous growth. Its canes are medium caliper to heavy.

The color of the main stems is near Light Olive, 10Y5/5. There are several medium-length large prickles which are almost straight to hooked slightly downward, with medium-length to long moderately broad base. The color of the prickles is gray to near Moderate Reddish Brown, 10R3/4. There are from few to several small prickles of the same coloration as the large prickles. There are no hairs.

The branches are between Moderate Yellow Green, 5GY5/6, and Moderate Olive Green, 5GY4/3, in color. They bear from few to several large prickles which are medium-length and hooked downward, with medium-length moderately broad base. The color of the prickles ranges between Moderate Brown, 7.5YR4/5, and Moderate Reddish Brown, 10R3/4. There are a few small prickles of about the same coloration as the large prickles. There are no hairs.

New shoots are near Strong Yellow Green, 5GY6/8, in color, moderately overlaid with near Dark Red, 5R3/7, especially where exposed to light. There are a few large prickles which are moderatly short to medium-length, hooked slightly downward, and with medium-length narrow base. The color of the large prickles is near Strong Yellow Green, 2.5GY6/8, at the tips, the remainder being overlaid with near Dark Red, 5R3/7. There are a few small prickles of the same coloration as the large prickles. There are no hairs.

I claim:

1. A new and distinct variety of hybrid tea rose, substantially as described and illustrated herein, said plant being characterized by a very vigorous upright-spreading to semi-climbing habit, which grows tall and bushy and has foliage of a medium olive-green color with leaflets tending to be somewhat folded inward bilaterally from the midrib, yet hanging downward from the rachis, the flowering of said plant being characterized in that its sepals turn down quickly as the bud begins to open, the blooms have double petalage of from about 25 to 34 petals with two to four petaloids; and the bloom spreads from 5 to 5½ inches, producing an overall color effect at first of a medium golden yellow, without significant other coloration, which lightens in shade as the bloom matures.

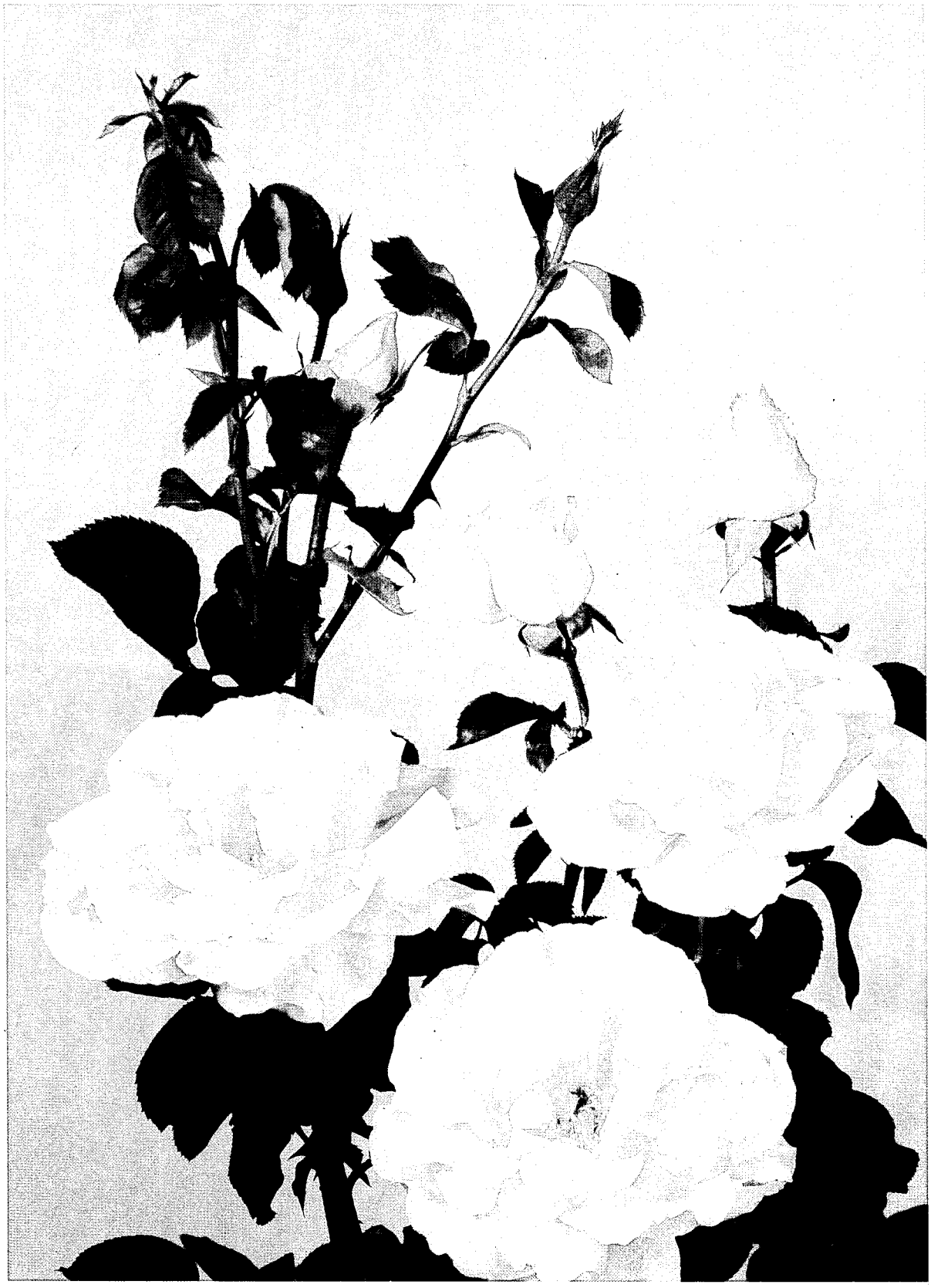

* * * * *